United States Patent
Heller et al.

(10) Patent No.: US 6,361,539 B1
(45) Date of Patent: *Mar. 26, 2002

(54) FILLING TRANSFER APPARATUS FOR BONE CEMENT

(75) Inventors: Mathias Heller, Winterthur; Fernando Suarez, Zurich, both of (CH)

(73) Assignee: Sulzer Orthopaedie AG, Baar (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/496,292

(22) Filed: Feb. 1, 2000

Related U.S. Application Data

(63) Continuation-in-part of application No. 09/382,081, filed on Aug. 24, 1999.

(30) Foreign Application Priority Data

Sep. 16, 1998 (EP) ............................................ 98810925

(51) Int. Cl.⁷ .................................................. A61F 2/46
(52) U.S. Cl. .............................. 606/93; 606/92; 606/94
(58) Field of Search ............................... 606/92, 93, 94

(56) References Cited

U.S. PATENT DOCUMENTS 4,966,601 A * 10/1990 Draenert ...................... 606/92

FOREIGN PATENT DOCUMENTS

| DE | 2801706 | | 2/1979 |
| DE | 3717134 | A1 | 9/1988 |
| EP | 0170120 | A1 | 2/1986 |
| EP | 0380867 | A1 | 8/1990 |
| EP | 0747114 | A1 | 12/1996 |
| WO | WO 87/05492 | | 9/1987 |
| WO | WO 90/13264 | | 11/1990 |

* cited by examiner

*Primary Examiner*—David O. Reip
(74) *Attorney, Agent, or Firm*—Townsend and Townsend and Crew LLP

(57) ABSTRACT

The invention shows a filling transfer apparatus for bone cement with a cylindrical, upwardly open mixing container (1) and a filling transfer piston (2) which can be inserted therein, which is removably connected to the sleeve (4) of a cement injector (3) and which has an opening (5) through which the mixed bone cement (6) can be transferred into the sleeve (4) through a pressing down of the filling transfer piston (2). In this an ejection piston (7) is inserted in the sleeve (4) and has an aperture (8) in the region of the opening (5) for the through-flowing cement which can be closed by a plug (9) after the removal of the cement injector (3).

15 Claims, 5 Drawing Sheets

FILLING TRANSFER APPARATUS FOR BONE CEMENT

Figure 1:
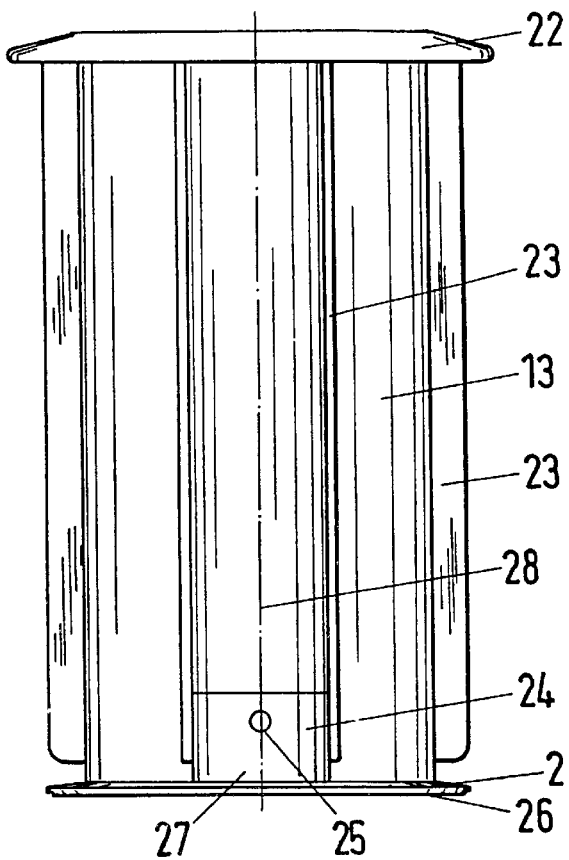

This application is a continuation-in-part of U.S. application Ser. No. 09/382,081, filed Aug. 24, 1999, the disclosure of which is incorporated by reference."

The invention relates to a filling transfer apparatus for bone cement with a cylindrical mixing container which is upwardly open and to a filling transfer piston which can be inserted therein, which is releasably connected to the sleeve of a cement injector and which has an opening through which the mixed bone cement can be transferred into the sleeve by a pressing down of the filling transfer piston.

A filling transfer apparatus of this kind is described in detail in EP-A-0 261 182. The latter however has the disadvantage that a filling transfer piston which is wetted by liquid bone cement must first be drawn out of a mixing container and must be disconnected from the actual injector in order to place on an ejection piston corresponding to the inner cross-section of the injector. In this, liquid bone cement should neither be sucked backwards nor spilled nor distributed to the surroundings.

The object of the invention is to improve this situation. This object is satisfied by the characterising features of the independent claim 1 in that an ejection piston, which has an aperture in the region of the opening for the through-flowing cement which can be closed by a plug after the removal of the cement injector, is inserted in the sleeve. This has the advantage that the dynamic seal which is actually distributed over a large periphery and is dimensioned for the pressing out is already installed when the bone cement enters into the injector, and that the smaller remaining aperture need only be statically sealed. In addition, the cross-section of the aperture can be matched to the viscosity of a preferred bone cement in such a manner that a backward flowing is largely prevented. Further improvements result through the subordinate claims 2 to 16. An aperture with a smallest passage area of less than 50 percent of the inner cross-section of the injection sleeve already brings about substantial improvements. In the case of a relatively fluid bone cement a passage area of between 25 and 5 percent of the inner cross-section of the injection sleeve has proved advantageous. In the case of such small apertures of the ejection piston the end of a piston rod of an ejection pistol can be provided with a plug which takes over the static sealing during the pressing out of the bone cement because the pressing force for the ejection piston is transferred via a substantially smaller surface than the piston surface. A frontal and possibly elastic shoulder which can adapt to the inclination of the piston surface of the ejection piston suffices as a static seal and has the advantage that hardened bone cement can be simply removed after use.

A further advantage results when the opening of the filling transfer piston is formed as a nozzle which protrudes into the aperture of the ejection piston. The actual restriction of the bone cement then takes place in the nozzle and only slight taking-along forces arise at the aperture and at the ejection piston during the transfer. When the opening of the nozzle on its outer side lies in contact at the ejection piston, it is prevented that the lower side of the ejection piston is wetted by the bone cement. In the removal of the injection sleeve and the ejection piston then, only a strand of viscous bone cement is still drawn between the nozzle and the aperture. A light pre-pressing between the nozzle and the ejection piston can be achieved when the ejection piston can be fixed in a lower position in the sleeve, for example through a snap connection which is force and form locked. A bulge which extends circumferentially in the cylindrical inner surface of the sleeve and which can only be displaced radially outwardly with a larger axial force at the ejection piston represents a snap connection of this kind.

A further advantage results when the filling transfer piston is blocked in its lower position in such a manner that the sleeve which is filled with cement and the partially closing-off ejection piston can be released from the filling transfer piston in this lower position. If an additional grip part which can still be gripped in the lower position is attached to the filling transfer piston, then a connection between the sleeve and the filling transfer piston can be released by hand in the lowest position of the filling transfer piston. In a rotational lock such as in a bayonet lock it suffices to rotate the grip part and the sleeve oppositely to one another. For a rotational lock, instead of a grip part, a rotational securing through projections and recesses can be attached in the lowest position between the filling transfer piston and the mixing container which transfers a torque from the mixing container to the filling transfer piston which is required for the release. Since with these measures the filling transfer piston need no longer be drawn out in order to release the sleeve, there is also no danger that bone cement is sucked back from the injector into the mixing container.

A grip part has the advantage that relatively large forces can be transmitted to the filling transfer piston for the transfer of the bone cement without a stressing of the connection between the sleeve and the filling transfer piston thereby arising. In addition the cross-section of the aperture and the nozzle can be chosen smaller when large forces can be transmitted to the filling transfer piston.

As concerns the handling, it is advantageous to provide the same kind of lock, for example a bayonet lock, between the sleeve and the filling transfer piston as between the sleeve and the ejection pistol. The sleeve with the bone cement remains in the same hand without a change of grip after the release from the filling transfer piston and can be placed onto the ejection pistol with an opposite movement.

A further functional advantage arises when the sleeve has a conical transition to a distributor tube and when this cone is repeated in the ejection piston and in the aperture as a nozzle. With this measure the outflow resistance to the distributor tube is lowered and the entire volume is pressed out into the distributor tube. In addition a stable guidance of the ejection piston is achieved when the force application of the piston takes place practically above the piston surface and above the sealing surface between the ejection piston and the sleeve. A short guide surface of the ejection piston in the sleeve, which can coincide with the sealing surface, suffices since with this suspension at the piston rod the ejection piston shows no tendency to tilt.

For practical reasons the mixing container can be executed as a transport container for one of the components of the bone cement so that a part which is designed as a throw-away part anyway fulfils a multiple function. A component of the bone cement in powder form can be enclosed in the mixing container for the transport by a cover or a tear-off foil. After the removal of the cover or the tear-off foil further components can be added and mixed by hand with a spatula. Then the filling transfer piston, on which the injector sleeve and the ejection piston were previously delivered in a pre-mounted condition, is placed on. After the mixing the operating personnel need only introduce and press down the filling transfer piston, release the sleeve from the filling transfer piston and place it on the ejector pistol, and this without applying sticky bone cement residues to the surfaces which can be gripped from the outside.

Figure 2:
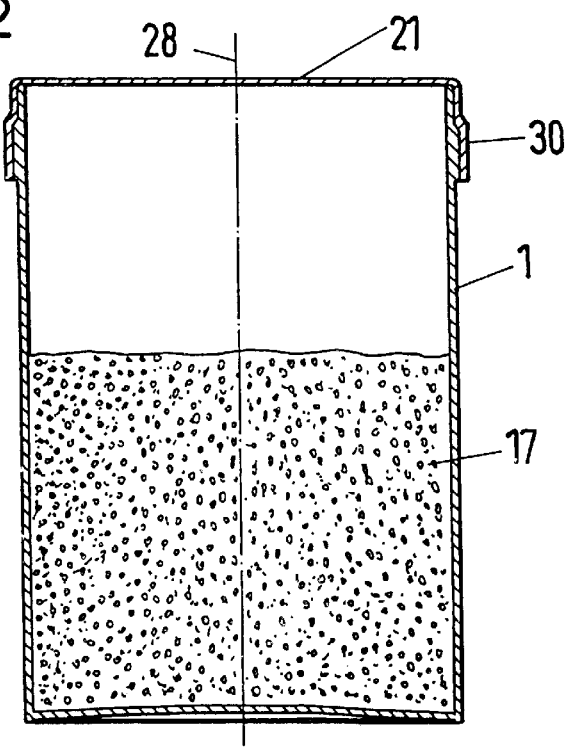
Figure 3:
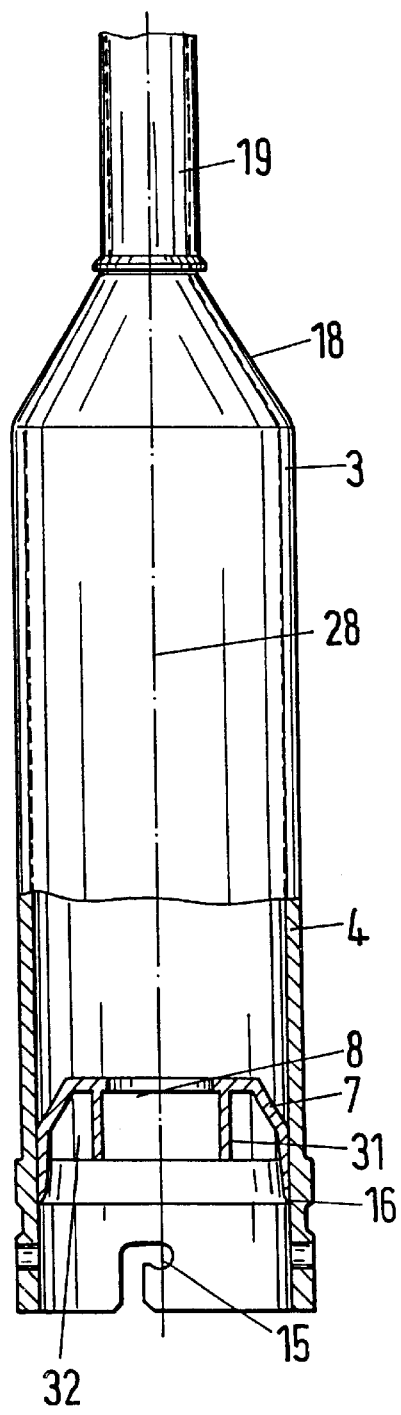
Figure 4:
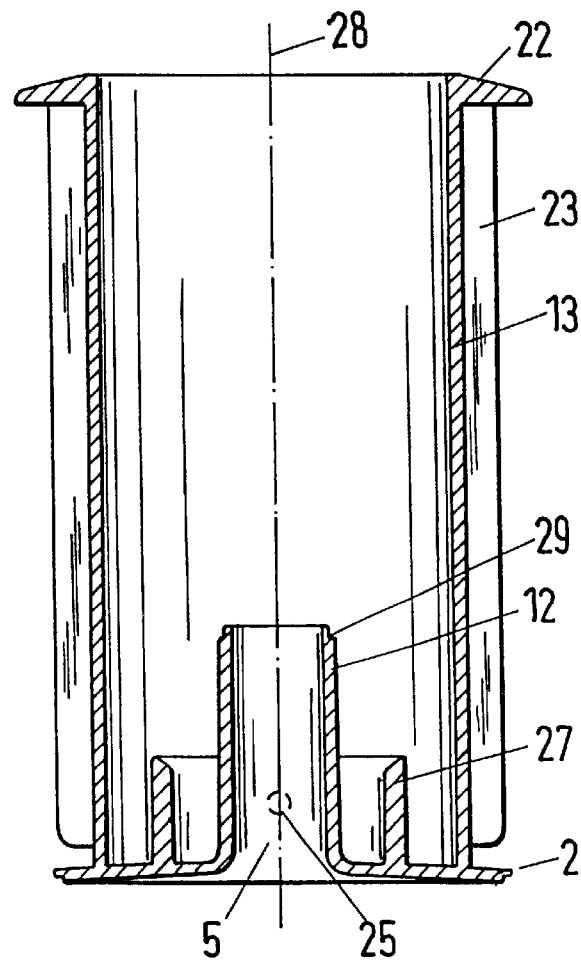
Figure 5:
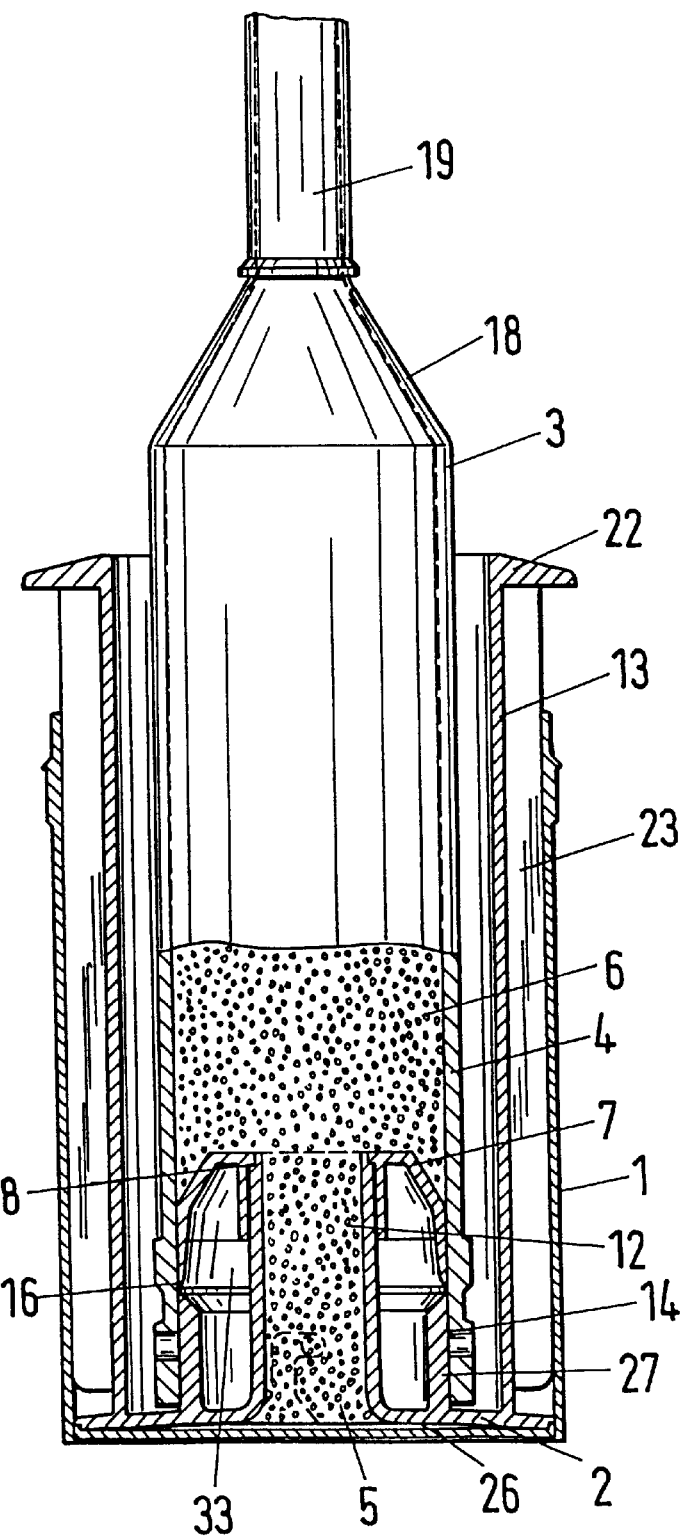
Figure 6:
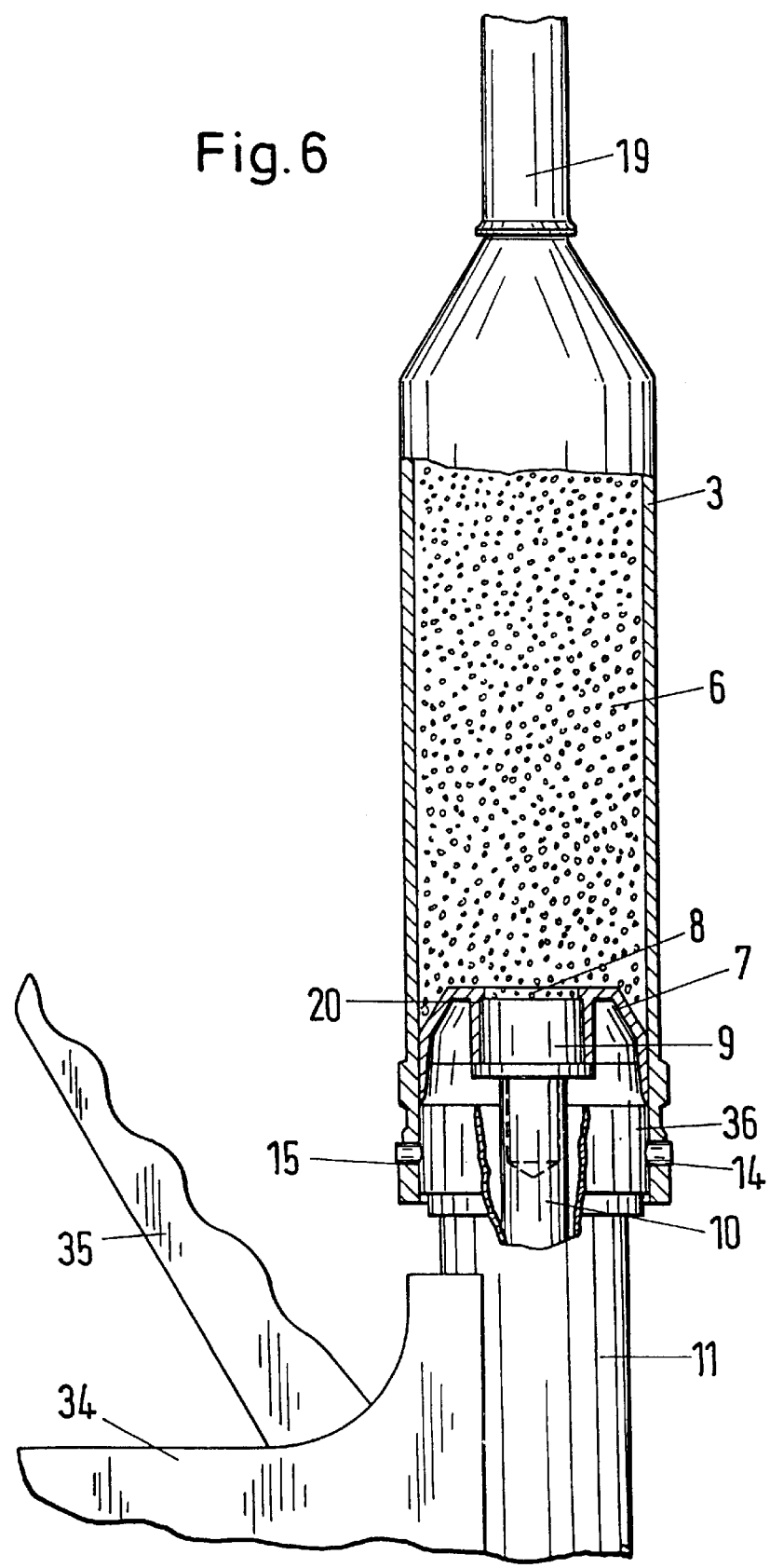
Figure 7:
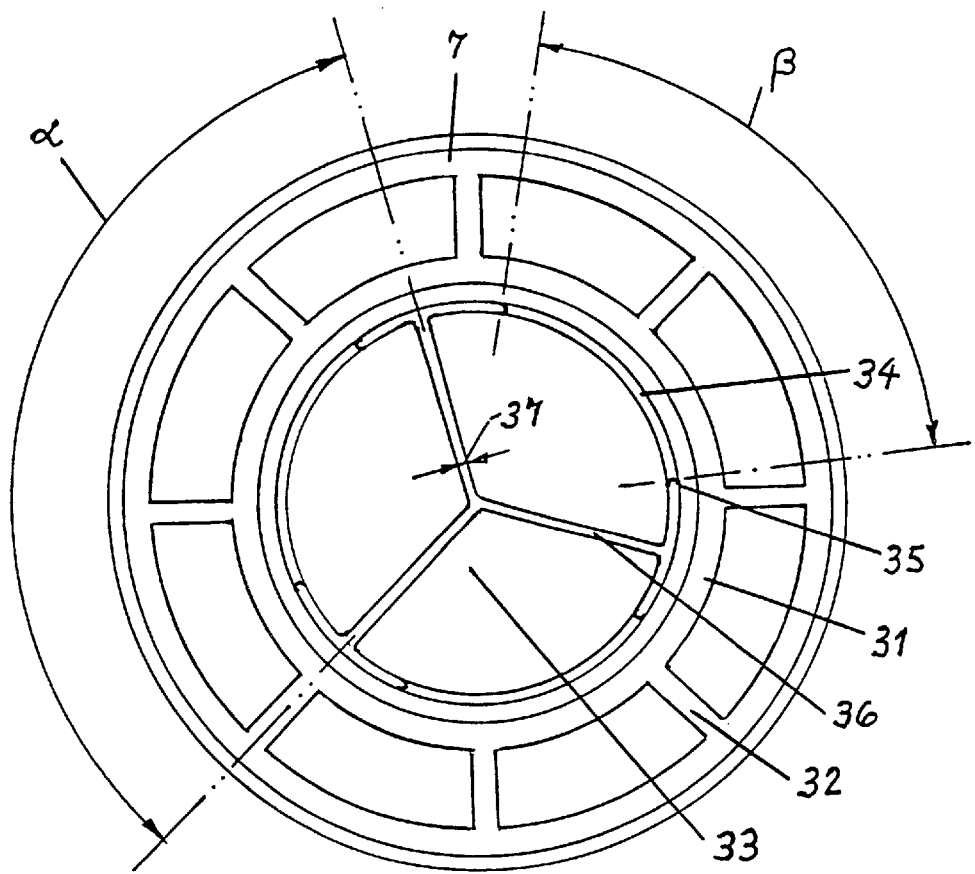
Figure 8:
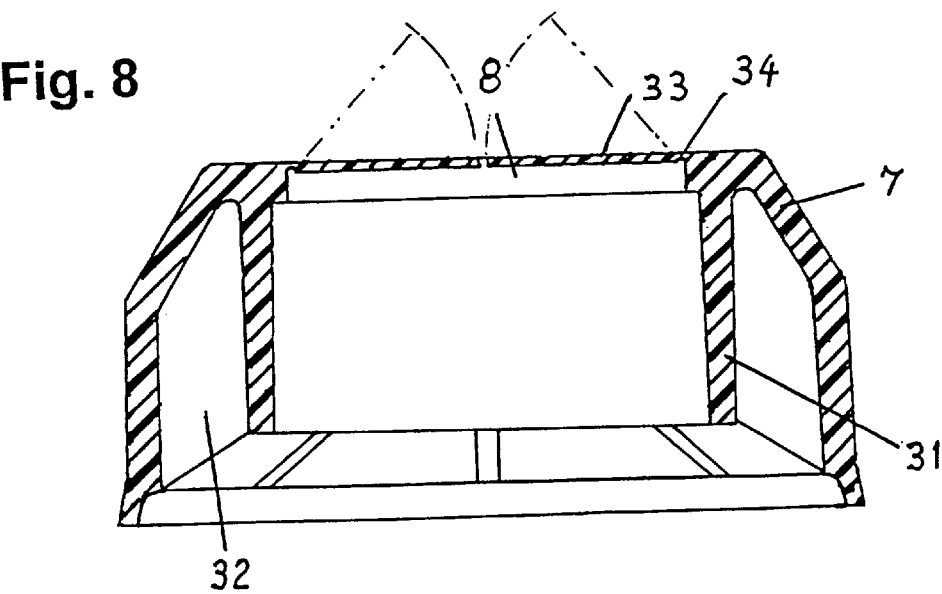

The invention will be described in the following with reference to an exemplary embodiment. Shown are:

FIG. 1 schematically, a view of a filling transfer piston with a grip part which has longitudinal ribs for the guidance of the actual piston;

FIG. 2 schematically, a longitudinal section through a mixing container which can initially be used as a transport container and after the mixing as a cylinder for the filling transfer piston in accordance with FIG. 1;

FIG. 3 schematically, a longitudinal section through a cement injector, in the sleeve of which an ejection piston with a central aperture is pre-mounted;

FIG. 4 schematically, a longitudinal section through a filling transfer piston of FIG. 1 in which an arrangement in accordance with FIG. 3 can be inserted with a bayonet lock;

FIG. 5 schematically in a longitudinal section, a filling transfer piston with a cement injector in its lowest position in the mixing container;

FIG. 6 schematically in a longitudinal section, the cement injector of FIG. 5 after the placing on onto an ejector pistol;

FIG. 7 schematically, an enlarged bottom view of an ejection piston in accordance with FIG. 3, which additionally has three flaps in it's aperture; and FIG. 8 schematically, a cross-section of the ejection piston of FIG. 7.

A filling transfer apparatus for bone cement with a cylindrical, upwardly open mixing container 1 and with a filling transfer piston 2 which can be inserted therein, which is removably connected to the sleeve 4 of a cement injector 3 and which has an opening 5 through which the mixed bone cement 6 can be transferred into the sleeve 4 through a pressing down of the filling transfer piston 2 is illustrated in the figures. Inserted in the sleeve 4 in this is an ejection piston 7 which has an aperture 8 in the region of the opening 5 for the through-flowing cement which can be closed with a plug after the removal of the cement injector 3.

The reference symbols in the figures are used for similar concepts. Since such parts as the mixing container 1, the lid 21, the filling transfer piston 2, the cement injector 3 with the sleeve 4 and with the ejection piston 7 are throw-away parts with large production numbers, these are as a rule manufactured of thermoplastics in injection moulding machines.

FIGS. 1 and 2 show a filling transfer piston 2 with an associated mixing container 1. The actual piston with the piston surface 26 is executed with thin walls and with a grip part 13 which consists of a tube section which is substantially taller than the mixing container 1 and which ends in a laterally protruding ring 22 at which the filling transfer piston can be pressed down by hand to the base of the mixing container 1. Longitudinal ribs 23 are distributed at the tube section over the periphery parallel to the longitudinal axis 28 and prevent, as guides, an inclined position of the piston surface 26 and its sealing edge in the mixing container. Two windows 24, which are displaced by 180°, are provided in the lower part of the tube section in order to be able to spout out in each case a pin 25 for a bayonet lock on a further inwardly lying ring 27 at laterally deformable tool punches.

The mixing container 1 is shown as a transport container which is closed by a lid 21 via a snap connection 30 in order to store and to transport components 17 of bone cement in powder form. For the production of the actual liquid bone cement the lid 21 is torn open at the side and removed. Then a liquid component is added to the powder component 17 from a separate vessel and the compound is stirred during a predetermined reaction time and mixed as uniformly as possible. The thus resulting bone cement 6, which is flowable for a limited time, must now be transferred into a cement injector 3.

The actual cement injector 3, which has a sleeve 4 with a conical transition 18 and a distributor tube 19, is shown in FIG. 3. The lower boundary of the sleeve 4 is reinforced outwardly and has four cut-outs for a bayonet lock 15. An ejection piston 7, of which the piston surface is matched to the inclination of the conical transition 18, is fixed in a lower position 16 by means of a slight modification (not shown) of the inner diameter of the sleeve 4. The ejection piston 7 has an aperture 8 in the centre which is matched to the outer dimensions of a nozzle 12 (FIG. 4). The ejection piston 7 receives a high stiffness against high pressing-on pressures through a support ring 31 and radial ribs 32. The fixing of the ejection piston 7 at the lower position 16 is dimensioned in such a manner that it can move upwardly only in the presence of a larger axial force.

The elements which are matched to the sleeve 4 and to the ejection piston 7 of the cement injector 3 are visible in FIG. 4. A guide ring 27 which is formed on at the piston base corresponds with its outer diameter to the inner diameter of the sleeve 4 and has two pins 25 which together with the cut-outs at the lower end of the sleeve 4 form a bayonet lock 15 which determines the axial position between the sleeve 4 and the filling transfer piston 2. Corresponding to this position and to the lower position 16 of the ejection piston 7 the opening 5 of the filling transfer piston 2 is formed to a nozzle 12 which protrudes into the ejection piston 7 and which with the actuation of the bayonet lock 15 lies in contact at the ejection piston 7 with a shoulder 29. The cement injector 3 with the ejection piston 7 and the filling transfer piston 2 are put together prior to the introduction of the filling transfer piston 2 into the mixing container 1 and locked relative to one another via the bayonet lock 15.

The locked unit of the filling transfer piston 2 and the cement injector 3 is gripped at the grip part 13 and pushed in from above into a mixing container 1 with fresh bone cement 6. When the bone cement 6 is encountered, the latter must be displaced through the mouth 12 into the cement injector 3. Corresponding to the diameter of the mouth 12 and to the momentary viscosity of the bone cement a corresponding axial force must be applied at the ring 22 until the filling transfer piston 2, as shown in FIG. 1, has reached the base of the mixing container 1. In FIG. 5 the nozzle 12 thrusts completely through the ejection piston 7 so that the bone cement 6 which flows into the sleeve 4 is uniformly distributed under the action of gravity in the sleeve 4 and slowly fills the latter, with the air above it being driven out through the distributor tube 19.

When the base is reached the bone cement 6 has been completely transferred into the cement injector 3 with the exception of a residual amount in the nozzle 12 and extends up into the distributor tube 19. In the case of a very fluid bone cement 6 a closure cap (not shown here) can be applied to the distributor tube 19 after the transfer in order to prevent a subsequent flowing of bone cement during the separation of the bayonet lock 15 between the filling transfer piston 2 and the cement injector 3. Beneath the ejection piston 7 there is a cavity 33 which is ventilated so well that air for a constriction and separation of the bone cement 6 in the aperture 8 can flow in when the bayonet lock 15 is released and when the cement injector 3 is pulled off at the partition location between the aperture 8 and the shoulder 29. For the release of the bayonet lock 15 the sleeve 3 is gripped at its upper region with one hand, while a corresponding counter-force is applied to the grip part 13, 22 with the other hand.

The cement injector 3 which has been drawn off is pushed onto an ejector pistol 11 as shown in FIG. 6. The latter has a piston rod 10 which can be moved out and onto which a plug 9 has been pushed on in order to seal off 20 the aperture 8 with the plug 9 and to transmit the ejection forces to the ejection piston 7. The piston rod 10 experiences, through a trigger lever 35 which is moved towards a pistol grip 34, a forward thrust movement which is strongly geared down in order to produce a large ejection force. For the transmission of a larger ejection force, pins engage at all four cut-outs of the sleeve 4 in order to form the bayonet lock 15. The large ejection force is necessary in order to overcome the cross-sectional reduction to the diameter of the distributor tube 19 and the friction at the distributor tube 19 and the sleeve 4. The pins are braced in a connection piece 36 which is matched, like the guide ring 27 in the filling transfer piston 2, to the inner diameter of the sleeve 4 in order to give the latter an orientation in the direction of the forward thrust movement of the piston rod 10.

Further improvements can be achieved by an ejection piston 7 as shown in FIGS. 7 and 8. Three flaps 33 project into the aperture 8 of the ejection piston 7 and cover nearly the complete cross-section of the aperture 8. Each flap 33 covers an angle α of 120 degree and is fixed with a hinge film 34 at it's periphery, whereby the hinge film 34 extends over an angle β of less than 90 degree and has radii 35 to prevent rupture of the film when the flaps elastically give way in axial direction. The flaps are separated from each other by small gaps 36, which have a width 37 of less than one millimeter. In the present example the angle β is 80 degree, the width 37 is 0.5 millimeter and the radii are 0.25 millimeter.

The flaps have the function to give way to the bone cement flowing into the cement injector 3. As soon as the flow stops, the flaps 33 swing back to their neutral position and prevent losses of bone cement, when the cement injector 3 is separated from the filling transfer piston 2.

What is claimed is:

1. A filling transfer apparatus for bone cement comprising:
    a cylindrical, upwardly open mixing container (1) to be filled with mixed bone cement (6);
    a filling transfer unit including a transfer piston (2) which can be inserted in the cylindrical, upwardly open mixing container (1);
    a cement injector (3) having a sleeve (4) and an ejection piston (7) with a smaller diameter than the transfer piston (2), the cement injector (3) being detachably removable from the transfer piston (2);
    the transfer piston (2) having an opening (5) which is formed as a nozzle (12) for completely penetrating the ejection piston (7) and for guiding the bone cement (6) into the sleeve (4) when the filling transfer unit is pressed down into the cylindrical, upwardly open mixing container (1);
    the filling transfer unit having a grip part (13) for removing the cement injector (3) by hand from the filling transfer unit.

2. The filling transfer apparatus in accordance with claim 1 wherein a smallest passage surface in the opening (5) corresponds to less than 50 percent of the inner cross-sectional surface of the sleeve (4).

3. The filling transfer apparatus in accordance with claim 1 wherein a smallest passage surface in the opening (5) corresponds to between 25 and 5 percent of an inner cross-sectional surface of the sleeve (4).

4. The filling transfer apparatus in accordance with claim 1 wherein the opening (5) is closed by a plug, which is a formed rod (10) as a constituent of an ejector pistol (11) which can be releasably connected to the sleeve (4).

5. The filling transfer apparatus in accordance with claim 1 wherein the ejection piston (7) can be fixed at a lower position (16) in the sleeve (4).

6. The filling transfer apparatus in accordance with claim 1 wherein the sleeve (4) and the filling transfer piston (2) are connectable through a rotational lock (14).

7. The filling transfer apparatus in accordance with claim 6 wherein the sleeve (4) is connectable with the same kind of lock both to the ejection piston (7) and to the ejector pistol (11).

8. The filling transfer apparatus in accordance with claim 6 wherein the filling transfer piston (2) is blocked against a rotation at least in its lowermost position in the mixing container (1).

9. The filling transfer apparatus in accordance with claim 1 wherein the filling transfer piston (2) has a grip part (13), which enables a moving of the filling transfer piston (2) by hand.

10. The filling transfer apparatus in accordance with claim 9 wherein the grip part (13) is provided with longitudinal ribs (23) to provide a guidance for the filling transfer piston (2) within the cylindrical, upwardly open mixing container (1).

11. The filling transfer apparatus in accordance with claim 1 wherein the mixing container (1) is executed as a closeable transport container for at least one of the components (17) of a bone cement (6) to be mixed.

12. The filling transfer apparatus in accordance with claim 11 wherein the mixing container (1) can be closed with a lid (21) or with a film for the transport of components of bone cement.

13. A filling transfer apparatus for bone cement comprising:
    a cylindrical, upwardly open mixing container (1);
    a filling transfer piston (2) which can be inserted in the cylindrical, upwardly open mixing container having an opening (5);
    a cement injector (3) having a sleeve (4) which is detachably removable connected to the filling transfer piston at the opening (5) through which the mixed bone cement (6) can be transferred into the sleeve (4) through a pressing down of the filling transfer piston (2);
    an ejection piston (7) inserted in the sleeve (4) with an aperture (8) in the region of the opening (5) for the through-flowing cement, the ejection piston (7) at the aperture 8 being capable of being closed by a plug (9) after the removal of the cement injector (3);
    an aperture (8) of the ejection piston (7) into which protrude more than two flaps (33) covering nearly the complete cross-section of the aperture (8), the flaps being fixed with a hinge film (34) at their periphery for giving way in axial direction.

14. The filling transfer apparatus in accordance with claim 13 with three flaps (33) covering each an angle α of 120 degrees, whereas the hinge film (34) extends at a reduced angle β of 80 degrees.

15. The filling transfer apparatus in accordance with claim 13 where the flaps are separated from each other by small gaps (36), which have a width (37) of less than one millimeter.

* * * * *